United States Patent
Pascal

(10) Patent No.: US 11,053,274 B2
(45) Date of Patent: *Jul. 6, 2021

(54) PROCESS FOR THE PRODUCTION OF ESTETROL INTERMEDIATES

(75) Inventor: Jean-Claude Pascal, Nice (FR)

(73) Assignee: ESTETRA S.P.R.L., Liege (BE)

( * ) Notice: Subject to any disclaimer, the term of this patent is extended or adjusted under 35 U.S.C. 154(b) by 285 days.

This patent is subject to a terminal disclaimer.

(21) Appl. No.: 14/122,872

(22) PCT Filed: Jun. 1, 2012

(86) PCT No.: PCT/EP2012/060447
§ 371 (c)(1),
(2), (4) Date: Nov. 27, 2013

(87) PCT Pub. No.: WO2012/164096
PCT Pub. Date: Dec. 6, 2012

(65) Prior Publication Data
US 2014/0107358 A1    Apr. 17, 2014

Related U.S. Application Data

(60) Provisional application No. 61/492,300, filed on Jun. 1, 2011.

(30) Foreign Application Priority Data

Jun. 1, 2011  (EP) .................................. 11168561

(51) Int. Cl.
*C07J 1/00* (2006.01)
*C07J 51/00* (2006.01)
*C07J 13/00* (2006.01)

(52) U.S. Cl.
CPC ........... *C07J 1/0066* (2013.01); *C07J 1/0059* (2013.01); *C07J 13/005* (2013.01); *C07J 51/00* (2013.01); *Y02P 20/55* (2015.11)

(58) Field of Classification Search
CPC ........ C07J 1/0066; C07J 1/0059; C07J 1/007; C07J 13/005; C07J 51/00; A61P 5/00; A61P 5/30; Y02P 20/55

(Continued)

(56) References Cited

U.S. PATENT DOCUMENTS

| 3,138,588 A | 6/1964 | Smith |
| 3,177,206 A | 4/1965 | Smith et al. |

(Continued)

FOREIGN PATENT DOCUMENTS

| CL | 2005-01207 A1 | 6/2006 |
| CL | 2014-00802 A1 | 11/2014 |

(Continued)

OTHER PUBLICATIONS

Suzuki et al., "Synthesis of 15alpha-hydroxyestrogen 15-N-acetylglucosaminides." Steroids, vol. 60, pp. 277-284, 1995.*

(Continued)

*Primary Examiner* — Barbara P Badio
(74) *Attorney, Agent, or Firm* — Lathrop GPM LLP; James H. Velema, Esq.; Laura A. Labeots, Esq.

(57) ABSTRACT

The present invention relates to a process for the preparation of a compound of formula (I) said process comprising the steps of: a) reacting a compound of formula (II), with an acylating or a silylating agent to produce a compound of formula (III), wherein $P^1$ and $P^2$ are each independently a protecting group selected from $R^2-Si-R^3R^4$, or $R^1CO-$, wherein $R^1$ is a group selected from $C_{1-6}$alkyl or $C_{3-6}$cycloalkyl, each group being optionally substituted by one or more substituents independently selected from fluoro or $C_{1-4}$alkyl; $R^2$, $R^3$ and $R^4$ are each independently a group selected from $C_{1-6}$alkyl or phenyl, each group being optionally substituted by one or more substituents independently selected from fluoro or $C_{1-4}$alkyl; b) reacting the compound of formula (III) in the presence of palladium acetate or a derivative thereof to produce compound of formula (IV); and c) reacting the compound of formula (IV) with a reducing agent to produce compound of formula (I).

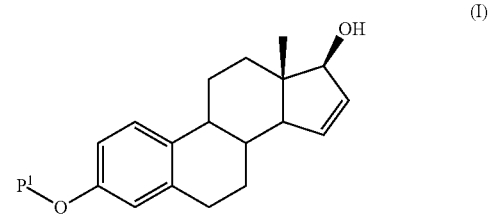

(I)

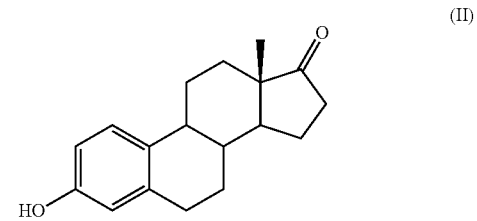

(II)

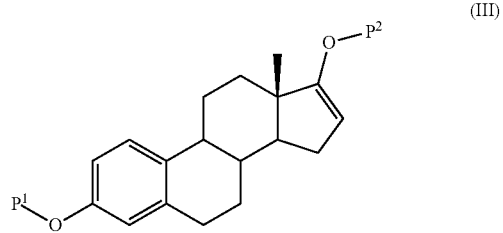

(III)

(Continued)

-continued

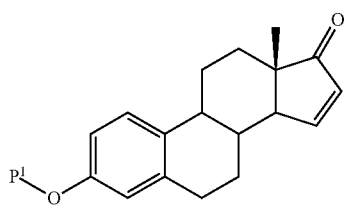

(IV)

9 Claims, No Drawings

(58) Field of Classification Search
USPC .................................................. 552/617, 625
See application file for complete search history.

(56) References Cited

U.S. PATENT DOCUMENTS

| | | | |
|---|---|---|---|
| 3,433,785 | A | 3/1969 | Phillips et al. |
| 4,739,078 | A | 4/1988 | Perlman |
| 4,792,620 | A | 12/1988 | Paulik |
| 4,923,640 | A | 5/1990 | Bohlmann et al. |
| 5,340,586 | A | 8/1994 | Pike et al. |
| 6,117,446 | A | 9/2000 | Place |
| 6,541,465 | B2 | 4/2003 | Loozen |
| 6,723,348 | B2 | 4/2004 | Faham et al. |
| 7,723,320 | B2 | 5/2010 | Bunschoten et al. |
| 7,732,430 | B2 | 6/2010 | Bunschoten et al. |
| 7,871,995 | B2 | 1/2011 | Bunschoten et al. |
| 7,923,440 | B2 | 4/2011 | Bunschoten et al. |
| 7,943,604 | B2 | 5/2011 | Coelingh Bennink et al. |
| 8,026,228 | B2 | 9/2011 | Coelingh Bennink et al. |
| 8,048,869 | B2 | 11/2011 | Bunschoten et al. |
| 8,236,785 | B2 | 8/2012 | Coelingh Bennink et al. |
| 8,367,647 | B2 | 2/2013 | Coelingh Bennink et al. |
| 8,518,923 | B2 | 8/2013 | Visser et al. |
| 8,987,240 | B2 | 3/2015 | Coelingh Bennink et al. |
| 8,987,484 | B2 | 3/2015 | Pascal et al. |
| 9,034,854 | B2 | 5/2015 | Coelingh Bennink et al. |
| 9,040,509 | B2 | 5/2015 | Coelingh Bennink et al. |
| 9,238,035 | B2 | 1/2016 | Foidart et al. |
| 9,561,238 | B2 | 2/2017 | Coelingh Bennink et al. |
| 9,579,329 | B2 | 2/2017 | Wouters et al. |
| 9,603,860 | B2 | 3/2017 | Perrin et al. |
| 9,808,470 | B2 | 11/2017 | Foidart et al. |
| 9,884,064 | B2 | 2/2018 | Platteeuw et al. |
| 9,987,287 | B2 | 6/2018 | Platteeuw et al. |
| 9,988,417 | B2 | 6/2018 | Gil et al. |
| 2004/0192620 | A1 | 9/2004 | Bunschoten et al. |
| 2004/0198671 | A1 | 10/2004 | Bunschoten et al. |
| 2005/0032755 | A1 | 2/2005 | Van Look et al. |
| 2005/0070488 | A1 | 3/2005 | Coelingh Bennik et al. |
| 2005/0147670 | A1 | 7/2005 | Hsu et al. |
| 2006/0063723 | A1 | 3/2006 | Coelingh Bennink et al. |
| 2006/0211669 | A1 | 9/2006 | Verhaar et al. |
| 2006/0276414 | A1 | 12/2006 | Coelingh Bennink et al. |
| 2007/0048369 | A1 | 3/2007 | Foreman et al. |
| 2007/0286819 | A1 | 12/2007 | De Vries et al. |
| 2008/0113953 | A1 | 5/2008 | De Vries et al. |
| 2011/0250274 | A1 | 10/2011 | Shaked et al. |
| 2014/0107091 | A1 | 4/2014 | Pascal et al. |
| 2014/0107358 | A1 | 4/2014 | Pascal et al. |
| 2014/0235882 | A1 | 8/2014 | Platteeuw et al. |
| 2015/0045300 | A1 | 2/2015 | Ahuja et al. |
| 2015/0105362 | A1 | 4/2015 | Verhaar et al. |
| 2015/0133413 | A1 | 5/2015 | Coelingh Bennink et al. |
| 2015/0182540 | A1 | 7/2015 | Heil et al. |
| 2016/0310506 | A1 | 10/2016 | Platteeuw et al. |
| 2016/0367567 | A1 | 12/2016 | Jaspart et al. |
| 2017/0196886 | A1 | 7/2017 | Wouters |
| 2017/0216318 | A1 | 8/2017 | Perrin et al. |
| 2017/0369521 | A1 | 12/2017 | Platteeuw et al. |
| 2018/0153801 | A1 | 6/2018 | Jaspart et al. |
| 2018/0169022 | A1 | 6/2018 | Jaspart et al. |
| 2018/0185271 | A1 | 7/2018 | Jaspart et al. |
| 2018/0265540 | A1 | 9/2018 | Verhaar et al. |

FOREIGN PATENT DOCUMENTS

| | | |
|---|---|---|
| CN | 1197387 A | 10/1998 |
| CN | 101443015 A | 5/2009 |
| CN | 101541326 A | 9/2009 |
| CN | 101631536 A | 1/2010 |
| CN | 102058604 A | 5/2011 |
| DE | 21 29 943 A1 | 12/1971 |
| DE | 144 266 A1 | 10/1980 |
| EP | 0277676 A | 8/1988 |
| EP | 0371466 A1 | 6/1990 |
| EP | 0646592 A1 | 4/1995 |
| EP | 2077272 | 7/2009 |
| EP | 2077273 | 7/2009 |
| EP | 2077322 A2 | 7/2009 |
| EP | 2077812 A2 | 7/2009 |
| EP | 2085373 A1 | 8/2009 |
| EP | 2383279 A1 | 11/2011 |
| EP | 3046928 A1 | 7/2016 |
| EP | 3106148 A1 | 12/2016 |
| JP | S63-216895 A | 9/1988 |
| JP | S63-258487 A | 10/1988 |
| JP | 2005-523283 T | 8/2005 |
| JP | 2010-513514 T | 4/2010 |
| WO | WO 2000/042955 A1 | 7/2000 |
| WO | WO 2001/005806 A2 | 1/2001 |
| WO | WO 2002/094275 A1 | 11/2002 |
| WO | WO 2002/094276 A1 | 11/2002 |
| WO | WO 2002/094278 A1 | 11/2002 |
| WO | WO 2002/094279 A1 | 11/2002 |
| WO | WO 2003/018026 A1 | 3/2003 |
| WO | WO 2003/041718 A1 | 5/2003 |
| WO | WO 2004/006936 A1 | 1/2004 |
| WO | WO2004/041839 A2 | 5/2004 |
| WO | WO 2004/103377 A1 | 12/2004 |
| WO | WO 2006/125800 A1 | 11/2006 |
| WO | WO 2007/081206 A1 | 7/2007 |
| WO | WO 2008/156365 A1 | 6/2008 |
| WO | WO 2010/033832 A2 | 3/2010 |
| WO | WO 2010/089078 A1 | 8/2010 |
| WO | WO 2012/164095 A1 | 12/2012 |
| WO | WO 2013/012326 A1 | 1/2013 |
| WO | WO 2013/021025 A1 | 2/2013 |
| WO | WO 2014/159377 A1 | 10/2014 |
| WO | WO 2015/086643 A1 | 6/2015 |
| WO | WO 2016/203006 A1 | 12/2016 |
| WO | WO 2016/203009 A1 | 12/2016 |
| WO | WO 2016/203044 A1 | 12/2016 |

OTHER PUBLICATIONS

International Preliminary Report on Patentability, PCT/EP2012/060447, dated Oct. 16, 2013, 10 pages.
Fishman et al: Synthesis of Epimeric 15-Hydroxyestriols, New and Potential Metabolites of Estradiol; J Org Chem; 1968, vol. 33, No. 8, pp. 3133-3135.
Li et al: Stereoselective synthesis of some methyl-substituted steroid hormones and their in vitro cytotoxic activity against human gastric cancer cell line MGC-803; Steroids; 2010, vol. 75, No. 12, pp. 859-869.
Larock, et al., "A Simple, Effective, New, Palladium-Catalyzed Conversion of Enol Silanes to Enones and Enals." Tetrahedron Letters. 1995, 36(14):2423-2426.
U.S. Appl. No. 14/122,872 / 2014/0107358, filed Nov. 27, 2013 / Apr. 17, 2014, Jean-Claude Pascal.
Cantrall et al. (1964) "The Synthesis of C-15 β-Substituted Estra-1,3,5(10)-trienes. I," J. Org. Chem. 29(1):64-68.
Cantrall et al. (1964) "The Synthesis of C-15 β-Substituted Estra-1,3,5(10)-trienes. II," J. Org. Chem. 29(1):214-217.

(56) References Cited

OTHER PUBLICATIONS

Egner et al. (1999) "7α,15α-Ethano bridged steroids. Synthesis and progesterone receptor interaction," Tetrahedron. 55:11267-11274.
Johnson et al. (1957) "14-Isoestrone Methyl Ether and its Identity with Totally Synthetic Material," J. Am. Chem. Soc. 79:2005-2009.
Minami et al. (1986) "New synthetic methods for α,β-unsaturated ketones, aldehydes, esters and lactones by the palladium-catalyzed reactions of silyl enol ethers, ketene silyl acetals, and enol acetates with allyl carbonates," Tetrahedron. 42:2971-2977.
Takahashi et al. (1984) "Palladium-catalyzed chirality transfer of 1,3-diene monoepoxides and its application to the synthesis of steroid side chains," Tetrahedron Letters. 25:1921-1924.
Takahashi et al. (1985) "Regio- and stereoselective introduction of 15β-hydroxy group and side chains to steroids by the palladium-catalyzed reaction of 1,3-diene monoepoxide," Tetrahedron. 41:5747-5754.
U.S. Appl. No. 15/982,284, filed May 17, 2018.
U.S. Appl. No. 15/737,227, filed Dec. 15, 2017.
U.S. Appl. No. 15/737,233, filed Dec. 15, 2017.
U.S. Appl. No. 10/478,262 / 2004/0198671 / U.S. Pat. No. 8,048,869, filed May 25, 2004 / Oct. 7, 2004 / Nov. 1, 2011, Evert Johannes Bunschoten.
U.S. Appl. No. 10/495,707 / 2005/0070488 / U.S. Pat. No. 8,026,228, filed Nov. 16, 2004 / Mar. 31, 2005 / Sep. 27, 2011, Herman Jan Tijmen Coelingh Bennink.
U.S. Appl. No. 10/478,365 / 2004/0198710 / U.S. Pat. No. 7,732,430, filed May 25, 2004 / Oct. 7, 2004 / Jun. 8, 2010, Evert Johannes Bunschoten.
U.S. Appl. No. 10/478,357 / 2004/0192620 / U.S. Pat. No. 7,871,995, filed May 25, 2004 / Sep. 30, 2004 / Jan. 18, 2011, Evert Johannes Bunschoten.
U.S. Appl. No. 10/478,264 / 2004/0186086 / U.S. Pat. No. 7,723,320, filed May 25, 2004 / Sep. 23, 2004 / May 25, 2010, Evert Johannes Bunschoten.
U.S. Appl. No. 10/517,686 / 2005/0261209 / U.S. Pat. No. 7,923,440, filed Jun. 30, 2005 / Nov. 24, 2005 / Apr. 12, 2011, Evert Johannes Bunschoten.
U.S. Appl. No. 10/517,509 / 2005/0215538 / U.S. Pat. No. 7,943,604, filed Jun. 13, 2005 / Sep. 29, 2005 / May 17, 2011, Herman Jan Tijmen Coelingh Bennink.
U.S. Appl. No. 13/017,858 / 2011/0160173 / U.S. Pat. No. 9,040,509, filed Jan. 31, 2011 / Jun. 30, 2011 / May 26, 2015, Herman Jan Tijmen Coelingh Bennink.
U.S. Appl. No. 10/521,040 / 2006/0063723 / U.S. Pat. No. 9,034,854, filed Aug. 16, 2005 / Mar. 23, 2006 / May 19, 2015, Herman Jan Coelingh Bennink.
U.S. Appl. No. 14/600,795 / 2015/0133413, filed Jan. 20, 2015 / May 14, 2015, Herman Jan Tijmen Coelingh Bennink.
U.S. Appl. No. 10/532,320 / 2006/0247221 / U.S. Pat. No. 8,987,240, filed Jun. 2, 2006 / Nov. 2, 2006 / Mar. 24, 2015, Herman Jan Tijmen Coelingh Bennink.
U.S. Appl. No. 14/621,267 / 2015/0150887 / U.S. Pat. No. 9,561,238, filed Feb. 12, 2015 / Jun. 4, 2015 / Feb. 7, 2017, Herman Jan Tijmen Coelingh Bennink.
U.S. Appl. No. 10/557,549 / 2006/0276414, filed May 22, 2006 / Dec. 7, 2006, Herman Jan Tijmen Coelingh Bennink.
U.S. Appl. No. 12/522,313 / 2010/0113346 / U.S. Pat. No. 8,236,785, filed Jul. 7, 2009 / May 6, 2010 / Aug. 7, 2012, Herman Jan Tijmen Coelingh Bennink.
U.S. Appl. No. 12/664,982 / 2010/0184736 / U.S. Pat. No. 8,367,647, filed Dec. 30, 2009 / Jul. 22, 2010 / Feb. 5, 2013, Herman Jan Tijmen Coelingh Bennink.
U.S. Appl. No. 12/669,778 / 2010/0184731 / U.S. Pat. No. 8,518,923, filed Apr. 2, 2010 / Jul. 22, 2010 / Aug. 27, 2013, Monique Visser.
U.S. Appl. No. 10/534,079 / 2006/0211669, filed Nov. 14, 2005 / Sep. 21, 2006, Mark Theodoor Verhaar.
U.S. Appl. No. 14/578,137 / 2015/0105362, filed Dec. 19, 2014 / Apr. 16, 2015, Mark Theodoor Verhaar.
U.S. Appl. No. 14/233,362 / 2014/0235882, filed Apr. 3, 2014 / Aug. 21, 2014, Johannes Jan Platteeuw.
U.S. Appl. No. 15/426,209 / 2017/0369521, filed Feb. 7, 2017 / Dec. 28, 2017, Johannes Jan Platteeuw.
U.S. Appl. No. 14/122,892 / 2014/0107091, filed Nov. 27, 2013 / Apr. 17, 2014, Jean-Claude Pascal.
U.S. Appl. No. 14/349,940 / 2014/0243539 / U.S. Pat. No. 8,987,484, filed Apr. 4, 2014 / Aug. 28, 2014 / Mar. 24, 2015, Jean-Claude Pascal.
U.S. Appl. No. 14/238,310 / 2014/0200202 / U.S. Pat. No. 9,579,329, filed Feb. 11, 2014 / Jul. 17, 2014 / Feb. 28, 2017, Wout Wouters.
U.S. Appl. No. 15/405,968 / 2017/0196886, filed Jan. 13, 2017 / Jul. 13, 2017, Wout Wouters.
U.S. Appl. No. 15/103,180 / 2016/0310506 / U.S. Pat. No. 9,884,064, filed Jun. 9, 2016 / Oct. 27, 2016 / Feb. 6, 2018, Johannes Jan Platteeuw.
U.S. Appl. No. 15/852,187 / 2018/0117063 / U.S. Pat. No. 9,987,287, filed Dec. 22, 2017 / May 3, 2018 / Jun. 5, 2018, Johannes Jan Platteeuw.
U.S. Appl. No. 15/737,227, filed Dec. 15, 2017, Séverine Francine Isabelle Jaspart.
U.S. Appl. No. 15/737,189 / 2018/0153801, filed Dec. 15, 2017 / Jun. 7, 2018, Séverine Francine Isabelle Jaspart.
U.S. Appl. No. 15/737,233, filed Dec. 15, 2017, Séverine Francine Isabelle Jaspart.
U.S. Appl. No. 15/185,337 / 2016/0367567, filed Jun. 17, 2016 / Dec. 22, 2016, Séverine Francine Isabelle Jaspart.
U.S. Appl. No. 14/395,465 / 2015/0133419 / U.S. Pat. No. 9,238,035, filed Oct. 17, 2014 / May 14, 2015 / Jan. 19, 2016, Jean-Michel Foidart.
U.S. Appl. No. 14/963,676 / 2016/0101116 / U.S. Pat. No. 9,808,470, filed Dec. 9, 2015 / Apr. 14, 2016 / Nov. 7, 2017, Jean-Michel Foidart.
Al-Jefout et al., "Continuous Norethisterone Acetate versus Cyclical Drospirenone 3 mg/Ethinyl Estradiol 20 ug for the Management of Primary Dysmenorrhea in Young Adult Women," Journal of Pediatric and Adolescent Gynecology, vol. 29, No. 2, pp. 143-147, XP029421056, 2011.
Andersch and Milsom: "An epidemiologic study of young women with dysmenorrhea", Am J Obstet Gynecol, 144(6), p. 655-660, 1982.
Anderson and Spencer: "Risk factors for venous thromboembolism", Circulation, 107, I-9-I-16, 2003.
Anderson et al., "Effects of conjugated equine estrogen in postmenopausal women with hysterectomy" The Women's Health Initiative randomized controlled trial, JAMA, vol. 291(14), pp. 1701-1712, 2004.
Apter et al., "Bleeding pattern and cycle control with estetrol-containing combined oral contraceptives: results from a phase II, randomised, dose-finding study (FIESTA)", Contraception, 94(4), p. 366-373 (Oct. 2016), 2016.
Archer et al., "A randomized, double-blind, placebo-controlled study of the lowest effective dose of drospirenone with 17β-estradiol for moderate to severe vasomotor symptoms in postmenopausal women", Menopause, vol. 21(3), pp. 227-235, 2011.
Arnal et al., "Tissue specificity of the membrane vs nuclear actions of estrogen receptor alpha: insights from targeted mutations in mouse models," Archives of Cardiovascular Diseases Supplements, (Apr. 2016) vol. 8(3), p. 217, Abstract 0333, 2016.
Bagot et al., "The effect of estrone on thrombin generation may explain the different thrombotic risk between oral and transdermal hormone replacement therapy", J Thromb Haemost., 8(8):1736-1744, 2010.
Bennink et al. (2008) "Ovulation inhibition by estetrol in an in vivo model," Contraception. 77(3):186-190.
Bennink et al. (Apr. 2007) "Estetrol (E4), the forgotten fetal steroid," In; The Abstracts of the 9th European Congress of Endocrinology Meeting. Budapest, Hungary. vol. 14. Abstract No. S16.2.
Bennink et al., "Estetrol review: profile and potential clinical applications," Climacteric (2008) vol. 11, Suppl. 1, pp. 7-58, XP009194877.
Bennink et al., "Clinical effects of the fetal estrogen estetrol in a multiple-rising-dose study in postmenopausal women", Maturitas, Elsevier, Amsterdam, NL, vol. 91, 2016, pp. 93-100, XP029649879.

(56) References Cited

OTHER PUBLICATIONS

Bennink et al., "Pharmacokinetics of the fetal estrogen estetrol in a multiple-rising-dose study in postmenopausal women", Climacteric. 20(3), 2017, pp. 285-289.
Bennink et al., Pharmacodynamic effects of the fetal estrogen estetrol in postmenopausal women: results from a multiple-rising-dose study, Menopause 24(6), 2017, pp. 677-685.
Bianchi, "Estetrol: Desde un estrogeno fetal hasta el tratamiento de la menopausia", Rev Chil Obstet Ginecol, 74(2): 123-126, 2009.
Bjarnason et al.,"Acute and long-term estradiol kinetics in smoking postmenopausal women", Climacteric, vol. 15(5), pp. 449-454, 2012.
Bosworth et al., "Depressive symptoms, menopausal status, and climacteric symptoms in women at midlife", Psychosom Med., 63(4):603-8, 2001.
Bull et al. "Synthesis and structure-activity studies of 8a- and 9beta-analogues of 14, 17-ethanoestradiol" J. Chem. Soc., Perkin Trans. 1, 2000, pp. 1003-1013, 2000.
Cainelli G. et al Synthesis, pp. 45-47, 1989.
Chemical Land data sheet: LiAlH4 (lithium aluminum hydride), Mar. 12, 2011.
Chinese Office Action in corresponding Chinese Patent Application No. 2012/80026131.6, dated Mar. 12, 2015.
Clive D.L. et al., J. Org. Chem., vol. 56, pp. 3801-3814, 1991.
Dahlback et al., "Familial thrombophilia due to a previously unrecognized mechanism characterized by poor anticoagulant response to activated protein C: prediction of a cofactor to activated protein C", Proc Natl Acad Sci U S A., 90(3), p. 1004-1008, 1993.
Davis et al., "Oral contraceptives for dysmenorrhea in adolescent girls: a randomized trial", Obstet Gynaecol, 106(1): 97-104, 2005.
De Bastos et al., "Combined oral contraceptives: venous thrombosis", Cochrane Database Syst Rev, (3):CD010813, 2014.
Dinger et al., "Risk of venous thromboembolism and the use of dienogest- and drospirenone-containing oral contraceptives: results from a German case-control study", J Fam Plann Reprod Health Care, 36(3):123-129, 2010.
Dinger et al., *Effectiveness of Oral Contraceptive Pills in a Large U.S. Cohort Comparing Progestogen and Regimen*, Obstet. & Gynecol., 117(1):33-40 (2011).
Dinger et al., *Oral Contraceptive Effectiveness According to Body Mass Index, Weight, Age, and Other Factors*, Am. J. Obstet. Gynecol., 201:263e1-9 (2009).
Dionne P et al Steroids, vol. 62, pp. 674-681, 1997.
Dörwald, Side Reactions in Organic Synthesis, WILEY-VCH Verlag GmbH & Co. KGaA, Weinheim, Preface,. p. IX, 2005.
Duijkers et al., "Inhibition of ovulation by administration of estetrol in combination with drospirenone or levonorgestrel: Results of a phase II dose-finding pilot study", Eur J Contracept Reprod Health Care,.20(6), p. 476-489, 2015.
Duijkers et al., "A randomized study comparing the effect on Ovarian activity of a progestogen-only pill (POP) containing desogestrel and a new POP containing drospirenone in a 24/4 regimen", Euro. J. Contracept. & Repro. Health Care, 20(6):419-27 (2015).
Elger et al., "Conception and pharmacodynamics profile of drospirenone", Steriods, 68(10):891-905 (2003).
Endrikat et al., "A twelve-month comparative clinical investigation of two low-dose oral contraceptives containing 20 micrograms ethinylestradiol/75 micrograms gestodene and 20 micrograms ethinylestradio1/150 micrograms desogestrel, with respect to efficacy, cycle control and tolerance", Contraception, 52(4), p. 229-235, 1995.
Erkkola et al. (2005) "Role of progestins in contraception," Acta Obstet. Gynecol. Scand. 84(3):207-216.
Fine (2011) "Update on emergency contraception," Adv. Ther. 28(2):87-90.
Foidart, "Estetrol, the first human, physiological Selective Estrogen Receptor Modulator," Presented at Eur. Soc. Contraception & Reprod. Health, 14th Cong, 2nd Global Conf., 2016.
French "Dysmenorrhea", Am Fam Physician, 71(2): 285-291, 2005.
Gardouh et al., "Preparation and characterization of mucoadhesive buccal film for delivery of meloxicam", British J. of Pharmaceutical Research, 3(4): 743-766, 2013.
Green et al., "Compounds Related to the Steroid Hormones. Part II. The Action of Hydrogen Bromide on 2-Bromo-3-oxo-delta1-5alpha-Steroids." J. Chem. Soc., pp. 2532-2543, 1961.
Greene Protective Groups in Organic Chemistry, John Wiley & Sons, New York, pp. 44-46 and 53-55, 1999.
Greene, Theodora W. et al. Protective Groups in Organic Synthesis, 3rd edition, pp. 113-179, 1999.
Haque et al., "Development of polymer-bound fast-dissolving metformin buccal film with disintegrants", Int. J. of Nanomedicine, 10: 199-205, 2015.
Harel., "Dysmenorrhea in adolescents and young adults: an update on pharmacological treatments and management strategies," Expert Opinion on Pharmacotherapy, vol. 13 No. 15, pp. 2157-2170, XP055389783, 2012.
Harlow et al., "Executive summary of the Stages of Reproductive Aging Workshop + 10: addressing the unfinished agenda of staging reproductive aging", Menopause, vol. 19(4), 2012.
Harrington et al., "Cross-sectional association of endogenous steroid hormone, sex hormone-binding globulin, and precursor steroid levels with hemostatic factor levels in postmenopausal women", J Thromb Haemost., 15(1), p. 80-90, 2017.
Heathcock et al., "Synthesis of Sesquiterpene antitumor Lactones. 10. Total Synthesis of (+/-)-Parthenin." J. Am. Chem. Soc., 104, pp. 6081-6091, 1982.
Heinemann et al., International versions of the Menopause Rating Scale (MRS), Health Qual Life Outcomes, pp. 1:28, 2003.
Heinemann et al., The Menopause Rating Scale (MRS) as outcome measure for hormone treatment? A validation study, Health Qual Life Outcomes, pp. 2:67, 2004.
Heinemann et al., "The Menopause Rating Scale (MRS) scale: A methodological review", Health Qual Life Outcomes, pp. 2:45, 2004.
Hendrix and Alexander: "Primary dysmenorrhea treatment with a desogestrel-containing low-dose oral contraceptive", 66(6), p. 393-399, 2002.
Hilditch et al., "A menopause specific quality of life questionnaire: development and psychometric properties", Maturitas, vol. 24(3), pp. 161-175, 1996.
International Search Report with Written Opinion corresponding to International Patent Application No. PCT/ EP2012/065572, dated Nov. 15, 2012.
International Preliminary Report on Patentability Corresponding to International Patent Application No. PCT/ EP2012/065572, dated Oct. 9, 2013.
International Preliminary Report on Patentability, PCT/EP2012/060447, dated Oct. 16, 2013, 9 pages.
International Preliminary Report on Patentability, PCT/EP2012/060446, dated Dec. 2, 2013, 6 pages.
Jick et al., "Risk of idiopathic cardiovascular death and nonfatal venous thromboembolism in women using oral contraceptives with differing progestagen components", Lancet, 346(8990): p. 1589-1593, 1995.
Johnson, William S. and Johns, William F., "14-Isoestrone Methyl Ether and its Identity with Totally Synthetic Material", J. Am. Chem. Soc., vol. 79, pp. 2005-2009.
Kluft et al: "Reduced hemostatic effects with drospirenone-based oral contraceptives containing estetrol vs ethinyl estradiol", Contraception, vol. 95, No. 2, p. 140-147, 2017.
Lidegaard et al., "Hormonal contraception and risk of venous trhomboembolism: national follow-study", BMJ, 339:b2890, 2009.
Lidegaard et al., "Risk of venous thromboembolism from use of oral contraceptives containing different progestogens and oestrogen doses: Danish cohort study, Sep. 2001", BMJ, 343:d6423, 2011.
Liu et al, "5-(Trimethylstannyl)-2H-pyran-2-one and 3-(Trimethylstannyl)-2H-pyran-2-one: New 2H-Pyran-2-one Synthons", J Org Chem; 1996, vol. 61, No. 19, pp. 6693-6699.
Luo Lianmei et al., Major research advances in estetrol, J Reprod Med, vol. 18(3), pp. 305-308, 2009.
Magnus P et al J. Am. Chem. Soc., vol. 120, pp. 12486-12499, 1998.

(56) References Cited

OTHER PUBLICATIONS

Matsui M. et al. J. Chem. Soc., Perkin Trans. I, pp. 1429-1432, 2005.
Mawet et al., "Unique effects on hepatic function, lipid metabolism, bone and growth endocrine parameters of estetrol in combined oral contraceptives", Eur J Contracept Reprod Health Care, 20(6), p. 463-475, 2015.
Minami et al. (1964)"New synthetic methods for α,β-unsaturatedketones, aldehydes, esters and lactones by the palladium-catalyzed reactions of silyl enol eithers, ketene silyl acetals, and enol acetates with allyl carbonates," Tetrahedron. 42:2971-2977.
Mueller, George P et al. The Journal of Organic Chemistry, 26 (7), pp. 2403-2413.
Nambara T et al "Synthesis of Estetrol Monoglucuronides", Steroids, vol. 27, No. 1, pp. 111-122, XP009004815, 1976.
Nicolaou K.C. et al. Angewandte Chemie, vol. 41, No. 6, pp. 996-1000, XP002659963, 2002.
Norskov et al Nature Chemistry, 2009, 1, pp. 37-46, 2009.
Notelovitz et al., Initial 17β-Estradiol Dose for Treating Vasomotor Symptoms, Obstetrics and Gynaecology, vol. 95(5), pp. 726-731, 2000.
Odlind et al., "Can changes in sex hormone binding globulin predict the risk of venous thromboembolism with combined oral contraceptive pills?", Acta Obstet. Gynecol. Scand., 81(6), p. 482-490, 2002.
Ozanne et al. Organic Letters, vol. 5, No. 16, pp. 2903-2906, 2003.
Poirier D et al "Synthesis of 17beta-estradiol derivatives with N-Butyl, N-Methyl Alkylamide Side Chain at Position 15", Tetrahedron, vol. 47, No. 37, pp. 7751-7766, XP001122350, 1991.
Poort et al., "A common genetic variation in the 3'-untranslated region of the prothrombin gene is associated with elevated plasma prothrombin levels and an increase in venous thrombosis", Blood, 88(10), p. 3698-3703, 1996.
Portman et al., Genitourinary syndrome of menopause: new terminology for vulvovaginal atrophy from the International Society for the Study of Women's Sexual Health and the North American Menopause Society, Menopause, vol. 21(10), pp. 1063-1068, 2014.
Proctor and Farquhar: "Dysmenorrhoea", Clin Evid, 9, p. 1994-2013, 2007.
Reactivity Chart 1: Protection for Hydroxyl Group: Ethers, Greene's Protective Groups in Organic Synthesis, 3E, pp. 708-711, 1999.
Rodstrom et al., "A longitudinal study of the treatment of 25 hot flushes: the population study of women in Gothenburg during a quarter of a century", Menopause, vol. 9(3), pp. 156-161, 2002.
Rosenbaum et al., "Inhibition of ovulation by a novel progestogen (drospirenone) alone or in combination with ethinylestradiol", Euro. J. Contracept. & Repro. Health Care, 5(1):14-24 (2000).
Rosing et al., "Oral contraceptives and venous thrombosis: different sensitivities to activated protein C in women using second- and third-generation oral contraceptives", Br J Haematol., 97(1), p. 233-238, 1997.
Sakakibara M. et al Biosci. Biotech. Biochem., vol. 60, pp. 411-414, 1996.
Santoro, Symptoms of menopause: hot flushes, Clin Obstet Gynecol, vol. 51(3), pp. 539-548, 2008.
Savjani et al., "Drug solubility: importance and enhancement techniques", ISRN Pharm., 2012: 195727.
Sidney et al., "Recent combined hormonal contraceptives (CHCs) and the risk of thromboembolism and other cardiovascular events in new users", Contraception, 87(1), pp. 93-100, 2013.
Simon et al., "Menopausal hormone therapy for vasomotor symptoms: balancing the risks and benefits with ultra-low doses of estrogen", Expert Opin Investig Drugs, vol. 16(12), pp. 2005-2020, 2007.
Simoni et al., "The Discovery of Estrone, Estriol, and Estradiol and the Biochemical Study of Reproduction", the Work of Edward Adelbert Doisy, J. Biol. Chem., vol. 277, No. 28 e17, 2002.
Smith III et al. J. Org. Chem., vol. 72, pp. 4611-4620, 2007.
Smith III et al. Organic Letters, vol. 8, No. 10, pp. 2167-2170, 2006.
Spitzer et al., "Third generation oral contraceptives and risk of venous thromboembolic disorders: an international case-control study. Transnational Research Group on Oral Contraceptives and the Health of Young Women", BMJ, 312(7023), p. 83-88, 1996.
Strowitzki et al., "Efficacy of ethinylestradiol 20 μg/drospirenone 3 mg in a flexible extended reimen in women with moderate-to-severe primlary dysmenorrhea: an open-label, multicenter, ramdomised, controlled study," J. Fam. Plann. Reprod. Health Care (2012) vol. 38, pp. 94-101, 2012.
Sundell et al., "Factors influencing the prevalence and severity of dysmenorrhoea in young women.", Br J Obstet Gynaecol, 97(7), p. 588-594, 1990.
Takeuchi et al., "Solvent Effects and Steric Course in the Solvolysis of 1,3,3-Trimethyl-2-oxocyclopentyl mesylate in comparison with 1,1,3,3-Tetramethyl-2-oxobutyl System." Bull. Chem. Soc. Jpn., 74, pp. 363-370, 2001.
Tchaicovski and Rosing: "Mechanisms of estrogen-induced venous thromboembolism", Thromb Res., 126(1):5-11, 2010.
Trost et al., "Methyl 2-Pyridinesulfinate. A Convenient Reagent for Sulfinylation-Dehydrosulfinylation". Journal of Organic Chemistry. 1993, vol. 58, No. 6, pp. 1579-1581.
Utian et al., "Comparative controlled trial of a novel oral estrogen therapy, estradiol acetate, for relief of menopause symptoms", Menopause, vol. 12(6), pp. 708-715, 2005.
Visser et al. (2009) "Clinical applications for estetrol," J_ Steroid. Biochem. Mol. Biol. 114(1-2):85-89.
Vlieg et al: "The venous thrombotic risk of oral contraceptives, effects of oestrogen dose and progestogen type: results of the MEGA case-control study", BMJ, 339:b2921, 2009.
Wang et al., "Neurosteroid Analogues. Part 13: Synthetic methods for the Preparation of 2beta-Hydroxygonane Derivatives as Structural Mimics of ent-3alpha-Hydroxysteroid Modulators of GABA-A Receptors." Tetrahedron, 63, pp. 7977-7984, 2007.
Warmerdam et al., "A new route of synthesis of estetrol". Climacteric 2008, vol. 11, Suppl. 1, pp. 59-63.
Williams et al., "Strategies to address low drug solubility in discovery and development", Pharmacological Reviews, vol. 65(1), pp. 416-445, 2013.
Winkler et al., "Cycle control, quality of life and acne with two low-dose oral contraceptives containing 20 microg ethinylestradiol", Contraception, 96(6), p. 469-476, 2004.
Wong et al., "Oral contraceptive pill as treatment for pirmary dysmenorrhoea", Cochrane Database Syst Rev., CD002120, 2001.
Wto, "Venous thromboembolic disease and combined oral contraceptives: results of international multicentre case-control study", Lancet, 346(8990): p. 1575-1582, 1995.
Yamada et al., Specialty Chemicals Magazine, Catalysts, pp. 18-20.
Ylikorkala and Dawood, "New concepts in dysmenorrhea", Am J Obstet Gynecol, 130(7), p. 833-847, 1978.
Zhang and Wan Po, Efficacy of minor analgesics in primary dysmenorrhoea: a systematic review, 1998.

* cited by examiner

PROCESS FOR THE PRODUCTION OF ESTETROL INTERMEDIATES

RELATED APPLICATIONS

This application is a 35 U.S.C. § 371 filing of International Application No. PCT/EP2012/060447, filed Jun. 1, 2012; which claims priority to European Patent Application No. 11168561.6, filed on Jun. 1, 2011 and U.S. Provisional Patent Application No. 61/492,300, filed on Jun. 1, 2011. The entire contents of each are incorporated herein by reference.

FIELD OF THE INVENTION

The present invention relates to a new process for the synthesis of a key intermediate in the synthesis of Estetrol.

BACKGROUND OF THE INVENTION

Estrogenic substances are commonly used in methods of Hormone Replacement Therapy (HRT) and methods of female contraception. Estetrol is a biogenic estrogen that is endogenously produced by the fetal liver during human pregnancy. Recently, estetrol has been found effective as an estrogenic substance for use in HRT. Other important applications of estetrol are in the fields of contraception, therapy of auto-immune diseases, prevention and therapy of breast and colon tumors, enhancement of libido, skin care, and wound healing.

The synthesis of estetrol and derivatives thereof is known in the art. Verhaar M. T; et al (WO 2004/041839) describes a process for the preparation of estetrol starting from a 3-A-oxy-estra 1,3,5(10),15-tetraen-17-one, wherein A is an $C_1$-$C_5$alkyl group, or a $C_7$-$C_{12}$benzylic group. In this document, 3-A-oxy-estra 1,3,5(10),15-tetraen-17-ol is prepared in 6 steps from estrone where A is a benzyl group, the steps comprising protection of the 3-OH group by a benzyl group, then transformation of the 17-keto-group to a 17,17-ethylenedioxy derivative which is halogenated at the $C_{16}$ position using pyridinium bromide perbromide. Dehydrohalogenation is carried out by using potassium terbutoxyde in dimethylsulfoxide. Deprotection of the 17-keto-group is conducted using p-toluene-sulfonic acid monohydrate in aqueous acetone. Reduction of 17-keto-group affords the 17-ol derivative.

One of the disadvantages of the process described in WO 2004/041839 is the protection of 3-OH function with a benzyl group which can be removed only by hydrogenation using Pd/C as catalyst in the last steps of the estetrol synthesis. Furthermore the level of this catalyst in the final drug substance must be determined and must comply with the ICH guidelines.

Another disadvantage of the synthesis described in WO 2004/041839 is the two step protection/deprotection of the 17-keto function in order to generate the 15-16 double bond.

There remain a need for an improved synthesis of 3-Protected-oxy-estra-1,3,5(10),15-tetraene-17-ol.

It is therefore an object of the present invention to provide a process for the preparation of 3-Protected-oxy-estra-1,3,5 (10),15-tetraene-17-ol which overcome at least one the disadvantages of the prior art.

SUMMARY OF THE INVENTION

The present inventors have now found that this object can be obtained by using a process as defined in the appended claims.

According to a first aspect of the present invention, a process for the preparation of a compound of formula (I) (3-$P^1$-oxy-estra-1,3,5(10),15-tetraene-17-ol) is provided:

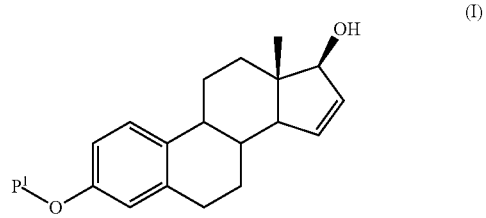

(I)

said process comprises the steps of:
a) reacting a compound of formula (II), with an acylating or a silylating agent to produce a compound of formula (III), wherein $P^1$ and $P^2$ are each independently a protecting group selected from $R^1CO$—, or $R^2$—Si—$R^3R^4$, wherein $R^1$ is a group selected from $C_{1-6}$alkyl or $C_{3-6}$cycloalkyl, each group being optionally substituted by one or more substituents independently selected from fluoro or $C_{1-4}$alkyl; $R^2$, $R^3$ and $R^4$ are each independently a group selected from $C_{1-6}$alkyl or phenyl, each group being optionally substituted by one or more substituents independently selected from fluoro or $C_{1-4}$alkyl;

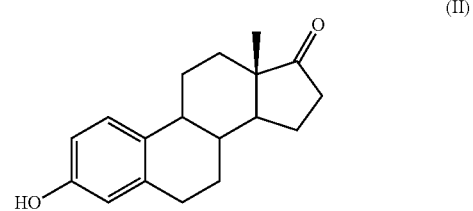

(II)

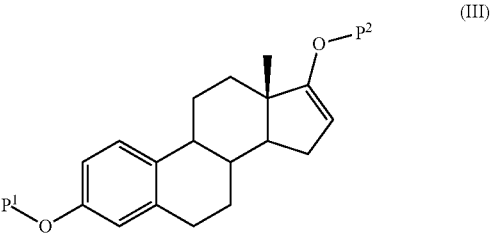

(III)

b) reacting the compound of formula (III) in the presence of palladium acetate or a derivative thereof to produce compound of formula (IV); and

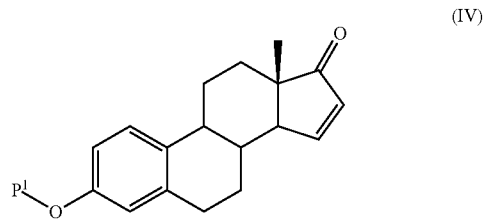

(IV)

c) reacting the compound of formula (IV) with a reducing agent to produce compound of formula (I).

Preferably, the present invention encompasses a process for the preparation of a compound of formula (I), said process comprising the steps of a) reacting a compound of formula (II), with an acylating or a silylating agent to produce a compound of formula (III), wherein $P^1$ and $P^2$ are each independently a protecting group selected from $R^2$—Si—$R^3R^4$, or $R^1$CO—, wherein $R^1$ is a group selected from $C_{1-6}$alkyl or $C_{3-6}$cycloalkyl, each group being optionally substituted by one or more substituents independently selected from fluoro or $C_{1-4}$alkyl; $R^2$, $R^3$ and $R^4$ are each independently a group selected from $C_{1-6}$alkyl or phenyl, each group being optionally substituted by one or more substituents independently selected from fluoro or $C_{1-4}$alkyl;

b) reacting the compound of formula (III) in the presence of palladium acetate present in catalytic or sub-stoichiometric amounts, in an oxygen atmosphere to produce compound of formula (IV); and c) reacting the compound of formula (IV) with a reducing agent to produce compound of formula (I).

The invention provides an improved process for producing 3-$P^1$-oxy-estra-1,3,5(10),15-tetraene-17-ol of formula (I) in significantly higher yield and/or at lower cost than possible by the previous known syntheses.

According to a second aspect, the present invention also encompasses a process for the preparation of estetrol, said process comprising preparing a compound of formula (I) by a process according to the first aspect of the invention and further reacting compound of formula (I) to produce estetrol.

According to a third aspect, the present invention also encompasses estetrol directly obtained by the process according to the second aspect of the invention, for use in a method selected from a method of hormone replacement therapy, a method of treating vaginal dryness, a method of contraception, a method of enhancing libido, of method of treating skin, a method of promoting wound healing, and a method of treating or preventing a disorder selected from the group consisting of autoimmune diseases, breast tumors and colorectal tumors.

The above and other characteristics, features and advantages of the present invention will become apparent from the following detailed description, which illustrate, by way of example, the principles of the invention.

DETAILED DESCRIPTION OF THE INVENTION

It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The term "alkyl" by itself or as part of another substituent, refers to a straight or branched saturated hydrocarbon group joined by single carbon-carbon bonds having 1 to 6 carbon atoms, for example 1 to 5 carbon atoms, for example 1 to 4 carbon atoms, preferably 1 to 3 carbon atoms. When a subscript is used herein following a carbon atom, the subscript refers to the number of carbon atoms that the named group may contain. Thus, for example, $C_{1-6}$alkyl means an alkyl of one to six carbon atoms. Examples of alkyl groups are methyl, ethyl, propyl, isopropyl, butyl, isobutyl, sec-butyl, tert-butyl, 2-methylbutyl, pentyl iso-amyl and its isomers, hexyl and its isomers.

The term "$C_{3-6}$cycloalkyl", as a group or part of a group, refers to a saturated cyclic alkyl radical containing from about 3 to about 6 carbon atoms. Examples of monocyclic $C_{3-6}$cycloalkyl radicals include cyclopropyl, cyclobutyl, cyclopentyl, or cyclohexyl.

The term "$C_{2-6}$alkenyl" by itself or as part of another substituent, refers to an unsaturated hydrocarbyl group, which may be linear, or branched, comprising one or more carbon-carbon double bonds. Examples of $C_{2-6}$alkenyl groups are ethenyl, 2-propenyl, 2-butenyl, 3-butenyl, 2-pentenyl and its isomers, 2-hexenyl and its isomers, 2,4-pentadienyl and the like.

The term "$C_{6-10}$aryl", by itself or as part of another substituent, refers to a polyunsaturated, aromatic hydrocarbyl group having a single ring (i.e. phenyl) or multiple aromatic rings fused together (e.g. naphthyl). or linked covalently, typically containing from 6 to 10 carbon atoms, wherein at least one ring is aromatic. $C_{6-10}$aryl is also intended to include the partially hydrogenated derivatives of the carbocyclic systems enumerated herein. Non-limiting examples of $C_{6-10}$aryl comprise phenyl, naphthyl, indanyl, or 1,2,3,4-tetrahydro-naphthyl.

The term "$C_{6-10}$aryl$C_{1-6}$alkyl", by itself or as part of another substituent, refers to a $C_{1-6}$alkyl group as defined herein, wherein one or more hydrogen atoms are replaced by one or more $C_{6-10}$aryl as defined herein. Examples of aralkyl radicals include benzyl, phenethyl, dibenzylmethyl, methylphenylmethyl, 3-(2-naphthyl)-butyl, and the like.

The term "$C_{1-6}$alkylcarbonyl", as a group or part of a group, represents a group of Formula —CO—$R^a$, wherein $R^a$ is $C_{1-6}$alkyl as defined herein.

The term "$C_{3-6}$cycloalkylcarbonyl", as a group or part of a group, represents a group of Formula —CO—$R^c$, wherein $R^a$ is $C_{3-6}$cycloalkyl as defined herein.

The term "$C_{2-6}$alkenyl$C_{1-6}$alkanoate" refers to a compound having the Formula $R^b$—O—CO—$R^a$ wherein $R^a$ is $C_{1-6}$alkyl as defined herein and $R^b$ is $C_{2-6}$alkenyl as defined herein.

The term "$C_{2-6}$alkenyl$C_{3-6}$cycloalkanoate" refers to a compound having the Formula $R^b$—O—CO—$R^c$ wherein $R^c$ is $C_{3-6}$cycloalkyl as defined herein and $R^b$ is $C_{2-6}$alkenyl as defined herein.

The term "$C_{1-6}$alkylenecarbonate" refers to a compound having the Formula $R^b$—O—CO—O—$R^a$ wherein $R^a$ is $C_{1-6}$alkyl as defined herein and $R^b$ is $C_{2-6}$alkenyl as defined herein.

The present invention relates to a process for preparing 3-$P^1$-oxy-estra-1,3,5(10),15-tetraene-17-ol of formula (I), wherein $P^1$ is a protecting group selected from $R^1CO$—, $R^2Si$—$R^3R^4$; wherein $R^1$ is a group selected from $C_{1-6}$alkyl or $C_{3-6}$cycloalkyl, each group being optionally substituted by 1, 2 or 3 substituents independently selected from fluoro or $C_{1-4}$alkyl; preferably $R^1$ is selected from the group comprising methyl, ethyl, propyl, isopropyl, butyl, isobutyl, tert-butyl, cyclopropyl, cyclobutyl, cyclopentyl, or cyclohexyl, each group being optionally substituted by 1, 2 or 3 substituents independently selected from fluoro or $C_{1-4}$alkyl; more preferably $R^1$ is methyl, ethyl, propyl, isopropyl, cyclopentyl, or cyclohexyl, yet more preferably $R^1$ is methyl, or ethyl;

$R^2$, $R^3$ and $R^4$ are each independently a group selected from $C_{1-6}$alkyl or phenyl, said $C_{1-6}$alkyl or phenyl, being optionally substituted with 1, 2 or 3 substituents independently selected from fluoro or $C_{1-6}$alkyl; preferably $R^2$, $R^3$ and $R^4$ are each independently selected from the group comprising methyl, ethyl, propyl, isopropyl, butyl, isobutyl, tert-butyl, and phenyl, each group being optionally substituted with 1, 2 or 3 substituents each independently selected from fluoro or $C_{1-4}$alkyl; preferably $R^2$, $R^3$ and $R^4$ are each independently selected from the group comprising methyl, ethyl, propyl, isopropyl, or tert-butyl, and phenyl, each group being optionally substituted with 1, 2 or 3 substituents each independently selected from fluoro or $C_{1-2}$alkyl,

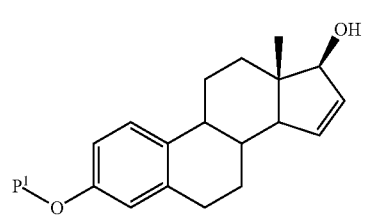

said process comprises the steps of
a) protecting the hydroxyl and the ketone of estrone of formula (II) to produce compound of formula (III), wherein $P^1$ is as defined above and $P^2$ is a protecting group selected from $R^1CO$—, $R^2$—Si—$R^3R^4$,

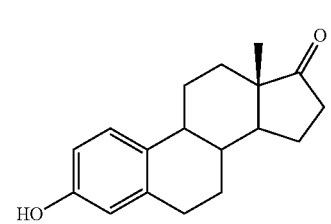

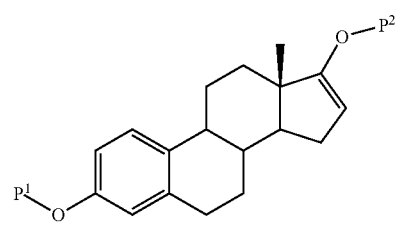

b) reacting the compound of formula (III) in the presence of palladium acetate or a derivative thereof such as palladium chloride or Tris(dibenzylideneacetone)dipalladium ($Pd_2(dba)_3$) to produce a compound of formula (IV), preferably in the presence of an oxygen atmosphere; and

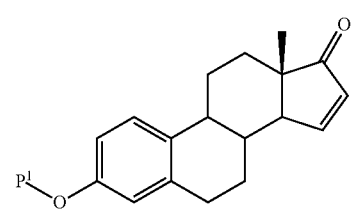

c) reacting the compound of formula (IV) with a reducing agent to produce compound of formula (I);
and if necessary any protective group used in the reactions described above is cleaved concurrently or subsequently; and
if desired, compound of formula (I) is subsequently converted into another compound by routine processes applicable for conversion of functional groups,
if desired a compound of formula I thus obtained is resolved into its stereoisomers.

In an embodiment, $P^1$ is $R^1CO$—; preferably $P^1$ is a group selected from $C_{1-4}$alkylcarbonyl or $C_{4-6}$cycloalkylcarbonyl, each group being optionally substituted by 1, 2 or 3 substituents independently selected from fluoro or $C_{1-4}$alkyl; more preferably $P^1$ is a group selected from $C_{1-2}$alkylcarbony or $C_{5-6}$cycloalkylcarbonyl, each group being optionally substituted by 1, 2 or 3 substituents independently selected from fluoro or $C_{1-2}$alkyl; for example $P^1$ is selected from acetyl, or cyclohexylcarbonyl, preferably $P^1$ is acetyl.

In an embodiment, $P^2$ is $R^1CO$—; preferably $P^2$ is a group selected from $C_{1-4}$alkylcarbonyl or $C_{4-6}$cycloalkylcarbonyl, each group being optionally substituted by 1, 2 or 3 substituents independently selected from fluoro or $C_{1-4}$alkyl; more preferably $P^2$ is a group selected from $C_{1-2}$alkylcarbony or $C_{5-6}$cycloalkylcarbonyl, each group being optionally substituted by 1, 2 or 3 substituents independently selected from fluoro or $C_{1-4}$alkyl; for example $P^2$ is selected from acetyl, or cyclohexylcarbonyl, preferably $P^2$ is acetyl.

In an embodiment, $P^1$ and $P^2$ are each independently $R^1CO$—.

In an embodiment, $P^1$ is $R^2$—Si—$R^3R^4$. Preferably $P^1$ is selected from the group comprising tert-butyl-dimethyl-silyl, diphenyl-methyl-silyl, dimethyl-phenyl-silyl, trimethyl-silyl, triethyl-silyl and triisopropyl-silyl, each group being optionally substituted by one or more substituents independently selected from fluoro or $C_{1-4}$alkyl; more preferably $P^1$ is tert-butyl-dimethyl-silyl.

In an embodiment, step (a) comprises the steps of (a1) protecting the hydroxyl of compound of formula (II) with a silylating agent to produce a compound of formula (IIa), wherein $P^1$ is $R^2$—Si—$R^3R^4$; and

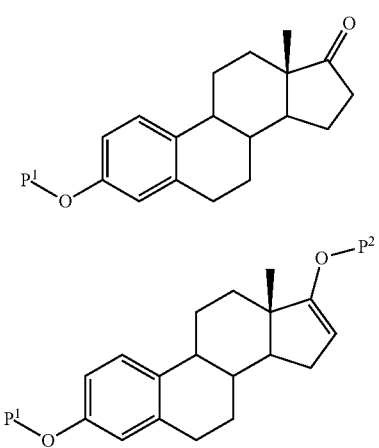

(a2) protecting the ketone of compound of formula (IIa) in the presence of an acylating agent to produce compound of formula (III), wherein $P^2$ is $R^1$CO—.

In an embodiment, $P^2$ is $R^2$—Si—$R^3R^4$; preferably $P^2$ is selected from the group comprising tert-butyl-dimethyl-silyl, diphenyl-methyl-silyl, dimethyl-phenyl-silyl, trimethyl-silyl, triethyl-silyl and triisopropyl-silyl, each group being optionally substituted by one or more substituents independently selected from fluoro or $C_{1-4}$alkyl, more preferably $P^2$ is tert-butyl-dimethyl-silyl.

In an embodiment, $P^1$ and $P^2$ are each independently $R^2$—Si—$R^3R^4$.

In an embodiment, $P^1$ is $R^2$—Si—$R^3R^4$; and $P^2$ is $R^1$CO—. Preferably $P^1$ is selected from the group comprising tert-butyl-dimethyl-silyl, diphenyl-methyl-silyl, dimethyl-phenyl-silyl, trimethyl-silyl, triethyl-silyl or triisopropyl-silyl, each group being optionally substituted by one or more substituents independently selected from fluoro or $C_{1-4}$alkyl; more preferably $P^1$ is tert-butyl-dimethyl-silyl; and preferably $P^2$ is a group selected from $C_{1-6}$alkylcarbonyl or $C_{3-6}$cycloalkylcarbonyl, each group being optionally substituted by 1, 2 or 3 substituents independently selected from fluoro or $C_{1-4}$alkyl; preferably $P^2$ is a group selected from $C_{1-4}$alkylcarbonyl or $C_{5-6}$cycloalkylcarbonyl; each group being optionally substituted by 1, 2 or 3 substituents independently selected from fluoro or $C_{1-2}$alkyl; more preferably $P^2$ is $C_{1-2}$alkylcarbony or $C_{5-6}$cycloalkylcarbonyl, for example $P^2$ is acetyl or cyclohexylcarbonyl, preferably acetyl.

In an embodiment, the silylating agent can be selected from the group comprising $C_{1-6}$alkylsilylchloride, $C_{1-6}$alkylsilyltriflate, phenylsilylchloride, phenylsilyltriflate, $C_{1-6}$alkylphenylsilylchloride, $C_{1-6}$alkylphenylsilyltriflate, each group being optionally substituted by one or more substituents independently selected from fluoro or $C_{1-4}$alkyl.

In an embodiment, the process for the preparation of 3-$P^1$-estra 1, 3, 5(10),15-tetraene-17-ol of formula (I) from estrone of formula (II) can be preformed in 3 steps as shown in Scheme 1. The compound of formula (I) can then be further reacted to prepare estetrol.

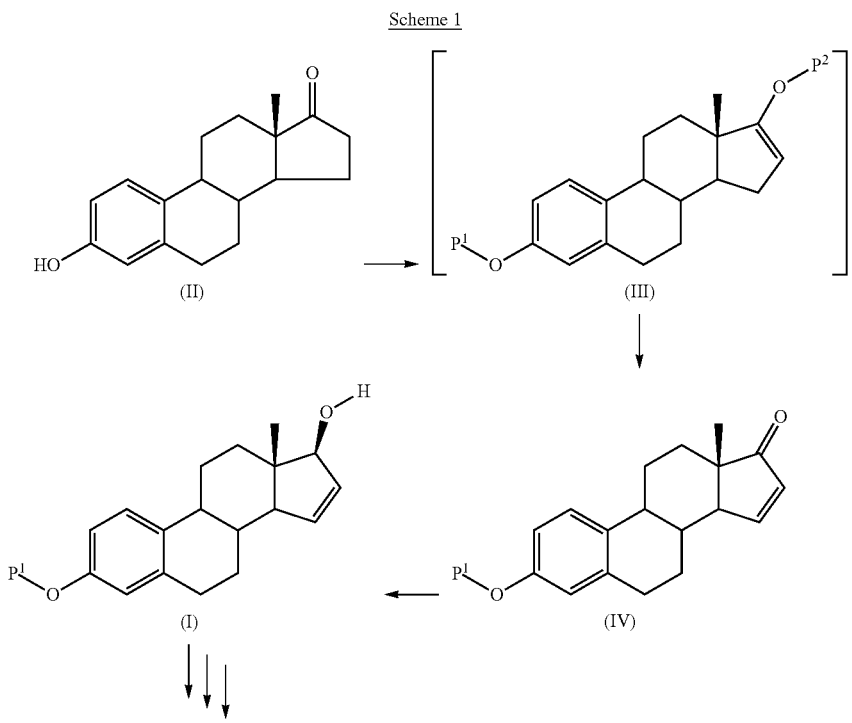

Scheme 1

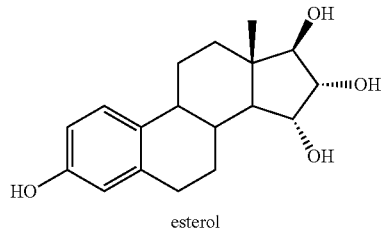
estetrol

According to scheme 1, the hydroxyl and the ketone of estrone of formula (II) are both protected, preferably in one step, to produce compound of formula (III).

In an embodiment, wherein $P^1$ and $P^2$ are each independently $R^1CO$—, estrone is reacted with an acylating agent. Preferably, said acylating agent is $C_{2-6}$alkenyl$C_{1-6}$alkanoate or $C_{2-6}$alkenyl$C_{3-6}$cycloalkanoate. Preferably, the acylating agent is selected from the group comprising $C_{2-6}$alkenylpropanoate, $C_{2-6}$alkenylbutanoate, $C_{2-6}$alkenylpentanoate, $C_{2-6}$alkenylhexanoate, $C_{2-6}$alkenylcyclopropanoate, $C_{2-6}$alkenylcyclobutanoate, $C_{2-6}$alkenylcyclopentanoate, and $C_{2-6}$alkenylcyclohexanoate. More preferably, the acylating agent is selected from the group comprising isopropenyl acetate, isopropenyl propionate, isopropenyl butyrate, isopropenyl isobutyrate, vinyl acetate, vinyl propionate, prop-2-enyl cyclohexanecarboxylate, ethenyl cyclopentanecarboxylate, and vinyl cyclohexanoate. More preferably, the acylating agent is selected from the group comprising isopropenyl acetate, isopropenyl propionate, isopropenyl butyrate, isopropenyl isobutyrate, vinyl acetate, and vinyl propionate.

The acylation can be performed in the presence of an acid, such as in the presence of sulfuric acid, or in the presence of a $C_{6-10}$arylsulfonic acid, optionally substituted by one or more chloro substituents. Non-limiting examples of a suitable acid include para-toluene sulfonic acid, and sulfuric acid.

For example, estrone of formula (II) can be was reacted with isopropenyl acetate in the presence of sulfuric acid or para-toluene sulfonic acid to give the estra-1,3,5(10),16-tetraene-3,17-diol,3,17-diacetate. The reaction can be performed under reflux, optionally under inert atmosphere, such as nitrogen atmosphere. The product can be used as such in the next step or further purified by known techniques in the art such as by chromatography, for example on silica with a suitable eluant such as methylene chloride/hexane or ethyl acetate/hexane.

In an embodiment, wherein $P^1$ and $P^2$ are each independently $R^2$—Si—$R^3R^4$, estrone of formula (II) is reacted with a silylating agent. The silylating agent can be selected from the group comprising $C_{1-6}$alkylsilyl triflate, phenylsilyltriflate, $C_{1-6}$alkylphenylsilyltriflate, $C_{1-6}$alkylsilylchloride, $C_1$phenylsilylchloride, $C_{1-6}$alkylphenylsilylchloride, each group being optionally substituted by one or more substituents independently selected from fluoro or $C_{1-4}$alkyl.

For example, formation of protected estrone silyl ether can be performed by reaction of a silylating agent such as tert-butyl dimethylsilyltriflate, diphenylmethylsilyltriflate, dimethylphenylsilyltriflate, trimethylsilyltriflate, triethylsilyltriflate, or triisopropylsilyltriflate. The reaction can be performed in the presence of a suitable base such as imidazole, 2,6-lutidine, collidine, triethylamine, or 1,8-diazabicyclo[5.4.0]undec-7-ene (DBU). The reaction can be performed at room temperature or under reflux. The reaction can be performed in the presence of a suitable solvent such as dichloromethane, toluene or dimethylformamide or a mixture thereof. The formation of protected estrone silyl ether can also be performed by reaction of a silylating agent such as tert-butyl dimethylsilylchloride, diphenylmethylsilylchloride, dimethylphenylsilylchloride, trimethylsilylchloride, triethylsilylchloride or triisopropylsilylchloride in the presence of a suitable base such as lithium diisopropylamide (LDA), tert-butyl lithium, sodium or potassium bis(trimethylsilyl)amide (NaHMDS, KHMDS) or lithium tetramethylpiperidine.

Step (b) of the present process comprises reacting the compound of formula (III) in the presence of palladium acetate or a derivative thereof such as palladium chloride or Tris(dibenzylideneacetone)dipalladium ($Pd_2(dba)_3$), preferably palladium acetate or palladium chloride, more preferably palladium acetate to produce a compound of formula (IV).

In an embodiment, said palladium acetate or a derivative thereof can be present in stoichiometric amounts, or sub-stoichiometric catalytic amounts.

For example the reaction of step (b) can be performed using stoichiometric amounts of palladium acetate, palladium chloride or Tris(dibenzylideneacetone)dipalladium, preferably stoichiometric amounts of palladium acetate, preferably in a suitable solvent such acetonitrile, benzonitrile or dimethylsulfoxide, preferably benzonitrile.

This reaction can be performed at room temperature.

In another example, said step (b) can be performed using sub-stoichiometric catalytic amounts of palladium acetate, palladium chloride, or Tris(dibenzylideneacetone)dipalladium, preferably sub-stoichiometric catalytic amounts of palladium acetate, in the presence of a $C_{1-6}$alkylene carbonate such as allyl carbonate and in the presence of an organotin compound as catalyst. Preferably, the organotin compound is tri-butyltin methoxide. Preferably the $C_{1-6}$alkylene carbonate is allyl methyl carbonate. The reaction can be performed under reflux conditions, optionally under inert atmosphere such as nitrogen or argon atmosphere.

In another example, said step (b) can be performed using sub-stoichiometric catalytic amounts of palladium acetate under an oxygen atmosphere. In another example, said step (b) can be performed using sub-stoichiometric catalytic amounts of palladium chloride, under an oxygen atmosphere. In another example, said step (b) can be performed using sub-stoichiometric catalytic amounts of Tris(dibenzylideneacetone)dipalladium, under an oxygen atmosphere.

Preferably, said oxygen atmosphere is pure molecular oxygen or atmospheric oxygen (air or circulating air, or renewable air).

Preferably, in step (b) the amount of palladium acetate, palladium chloride or Tris(dibenzylideneacetone)dipalladium is at most 0.50 equivalents, preferably at most 0.40 equivalents, more preferably at most 0.30 equivalents, yet more preferably at most 0.2 equivalents, yet more preferably at most 0.10 equivalents, yet more preferably at most 0.05 equivalents, yet more preferably at most 0.03 equivalents per equivalent of compound of formula (III).

In a preferred embodiment, step (b) is performed with at most 0.10 equivalents of palladium acetate, preferably at most 0.05 equivalents, preferably at most 0.03 equivalents per equivalent of compound of formula (III), in the presence of pure molecular oxygen or atmospheric oxygen.

The next step in the process comprises the reduction of the compound of formula (IV) with a reducing agent to produce compound of formula (I). Preferably, said reducing agent is a metal hydride compound. For example, the metal hydride compound can be selected from the group comprising $LiAlH_4$, $NaBH_4$, $NaBH(OAc)_3$, $ZnBH_4$, and $NaBH_4/CeCl_3$. preferably, said reducing agent is $NaBH_4/CeCl_3$.

For example said reduction can be performed in a suitable solvent or a mixture thereof, such as in tetrahydrofuran, or a mixture of methanol and tetrahydrofuran. The reaction can be performed at low temperatures such as below 15° C., for example below 10° C.

In an embodiment, compound of formula (IV) is not isolated but directly reduced to the alcohol using said reducing agent. In this embodiment, step (b) and (c) are performed in one pot. This one-pot/two-step procedure is the shortest chemical pathway described to obtain compound of formula (I).

This process offers the advantages that the 17-hydroxy function of the compound of formula (I) could be also protected by a protecting group such as an acyl group, more preferably an acetyl group which could be removed in the same time that the 3-protecting group such as 3-acetyl, preferably 3-acetoxy group offering a never described synthesis of estetrol in 6 steps. The 17-hydroxy function of the compound of formula (I) could be also protected by a silyl group, which could be removed in the same time that the 3-silyl protecting group offering a never described synthesis of estetrol in 6 steps.

According to another embodiment, step (a) can be performed in two steps and comprises the steps of (a1) protecting the hydroxyl of compound of formula (II) using a silylating agent to produce a compound of formula (IIa), wherein $P^1$ $R^2$—Si—$R^3R^4$; and

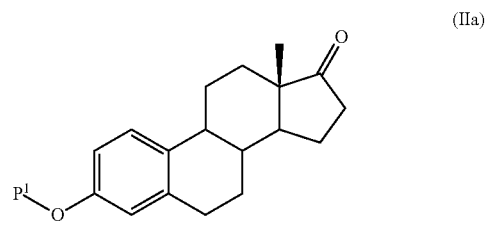

(a2) converting the ketone of compound of formula (IIa) to its enol ether in the presence of an acylating agent to produce a compound of formula (III).

According to this embodiment, the process for the preparation of 3-$P^1$-estra 1, 3, 5(10),15-tetraene-17-ol of formula (I) from estrone of formula (II) can be preformed as shown in Scheme 2.

Scheme 2

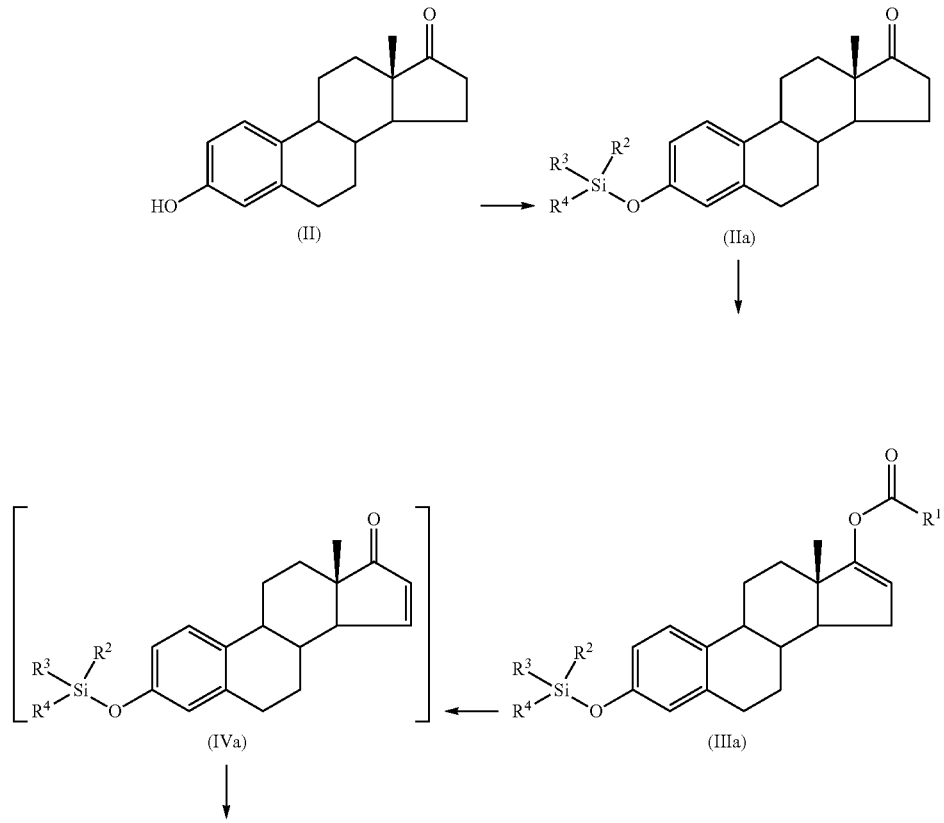

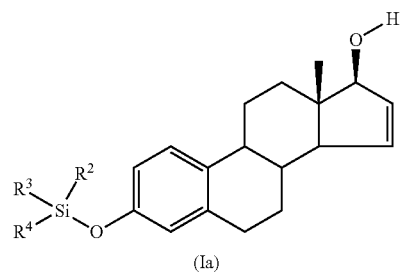

(Ia)

In this embodiment, illustrated in Scheme 2, wherein $P^1$ independently $R^2$—Si—$R^3R^4$, and $P^2$ is CO—$R^1$, estrone of formula (II) is reacted with a silylating agent to produce compound of formula (IIa). The silylating agent can be selected from the group comprising $C_{1-6}$alkylsilyl chloride, phenylsilyl chloride, $C_{1-6}$alkylphenylsilyl chloride; each group being optionally substituted by one or more substituents independently selected from fluoro or $C_{1-4}$alkyl.

For example, formation of protected estrone silyl ether can be performed by reaction of a silylating agent such as tert-butyl dimethylsilylchloride, diphenylmethylsilylchloride, dimethylphenylsilylchloride, trimethylsilylchloride, triethylsilylchloride, or triisopropylsilylchloride. The reaction can be performed in the presence of a base such as imidazole, 2,6-lutidine, collidine, triethylamine, or 1,8-diazabicyclo[5.4.0]undec-7-ene (DBU).

The next step comprises, converting the ketone of compound of formula (IIa) in the presence of an acylating agent to produce a compound of formula (II) wherein $P^2$ is acyl (compound of formula (IIIa)). Suitable acylating agents and conditions are as described herein above.

The next step in the process of scheme 2 comprises reacting the compound of formula (IIIa) in the presence of palladium acetate or a derivative thereof such as palladium chloride or Tris(dibenzylideneacetone)dipalladium ($Pd_2(dba)_3$) to produce compound of formula (IV) wherein $P^1$ is $R^2$—Si—$R^3R^8$ (IVa)). This reaction can be performed as described herein above.

The next step in the process comprises the reduction of the compound of formula (IVa) with a reducing agent to produce compound of formula (I) wherein $P^1$ is $R^2$—Si—$R^3R^4$ (compound of formula (Ia)). This reaction can be performed as described herein above.

The processes according to the present invention have the advantage that the protective group can be removed in situ at the end of the synthesis by conventional methods such as removal of silyl protecting group with fluoride ions, such as tetra-n-butylammonium fluoride; as described in Coppola, G. M. Org Prep Proced, 2007, 39 (2), 199-292 hereby incorporated by reference; or removal of silyl protecting groups using 2,3-dichloro-5,6-dicyano-p-benzoquinone as described in Tanemura, K. J Chem Soc, Perkin Trans 1 1992, (22), 2997-2998; hereby incorporated by reference.

The present process has the advantage that 3-$P^1$-oxy-estra-1,3,5(10),15-tetraen-17-ol of formula (I), and subsequently estetrol, can be obtained from estrone in a reduced number of steps compared to prior art processes, which is more convenient for an economical and industrial synthesis.

The present invention also encompasses a process for the preparation of estetrol, said process comprising preparing a compound of formula (I) using the process of the invention and further reacting compound of formula (I) to produce estetrol.

The present invention also encompasses the use of estetrol directly obtained by the process the invention for the manufacture of a pharmaceutical composition, preferably for use in a method selected from a method of hormone replacement therapy, a method of treating vaginal dryness, a method of contraception, a method of enhancing libido, of method of treating skin, a method of promoting wound healing, and a method of treating or preventing a disorder selected from the group consisting of autoimmune diseases, breast tumors and colorectal tumors.

The invention is illustrated but not limited by the following examples.

EXAMPLES

Example 1

Preparation of a Compound of Formula (I) Wherein $P^1$ is Acetyl According to an Embodiment of the Invention Step 1: Estra-1,3,5(10),16-tetraene-3,17-diol,3,17-diacetate 100 g of 3-hydroxy-estra-1,3,5(10)-trien-17-one (0.370 mole) was poured in 500 ml of isopropenyl acetate and 10 g of para-toluene-sulfonic acid. The mixture was refluxed. Acetone and isopropenyl acetate was continuously distilled off until the temperature reached 98° C. Then the mixture was cooled to 0° C. and $K_2CO_3$ was added.

After one hour at 0° C. the mixture was filtered, the resulting solution was concentrated and diisopropyl ether added. The precipitate was collected by filtration and dried. It weighted 111.5 g (yield: 85%)

$^1$HNMR (CDCl$_3$) δ 0.90 (s, 3H, $CH_3$ at C-18), 1.30-1.50 (m, 11H), 2.20 (s, 3H, $CH_3$ acetate), 2.30 (s, 3H, $CH_3$ acetate), 2.30-2.50 (m, 2H), 5.54 (broad s, 1H)), 6.80 (broad s, 1H, H4), 6.82 (dd, 1H, H2), 7.27 (d, 1H, H1) mp=148.3° C.

Step 2: 3-acetoxy-estra-1,3,5(10),15-tetraen-17-one

To a solution of 115.5 g (0.315 mole) of estra-1,3,5(10)-tetraene-3,17-diol,3,17, diacetate in 1500 ml of acetonitrile were added 30.4 g (0.095 mole) of tri-n-butyltin methoxyde and 11.2 g (0.05 mole) of palladium (II) acetate and allyl methyl carbonate 20 ml. The mixture was refluxed for 2 hours then cooled to room temperature and filtered through a pad of silica gel. The reaction was then diluted with water and extracted with ethyl acetate. After concentration to one third of the initial volume diisopropyl ether 1000 ml was slowly added. The precipitate was collected by filtration, washed with diisopropyl ether and used in the next step without further purification.

¹HNMR (CDCl₃) δ 1.10 (s, 3H, CH₃ at C-18), 1.30-2.60 (m, 9H), 2.30 (s, 3H, CH₃ 3-acetate), 2.90-3.00 (m, 2H), 6.00-6.15 (m, 1H, H15), 6.80 (broad s, 1H, H4), 6.85 (dd, 1H, H2), 7.29 (d, 1H, H1), 7.60 (d, 1H, H16), mp: 177.7° C.

Step 3: 3-acetoxy-estra-1,3,5(10),15-tetraene-17-ol

The collected material was dissolved in tetrahydrofuran (THF) 300 ml and a solution of cerium chloride heptahydrate (123 g, 0.33 mole) in methanol (300 ml) was added. The mixture was cooled to 0° C. and sodium borohydride (17.8 g, 0.47 mole, 1.5 q) was added portion wise keeping the temperature below 5° C. At this end of the addition, the mixture was stirred for one hour then quenched by addition of a 2N HCl solution (100 ml). The solution was partly evaporated in situ and water (4 L) was added. The precipitate was collected by filtration and dried. After crystallization form a mixture of ethanol/diisopropyl ether 3-acetoxy-estra-1,3,5(10),15-tetraene-17-ol was isolated in 75% yield.

¹HNMR (CDCl₃) δ 0.85 (s, 3H, CH₃ at C-18), 1.20-2.50 (m, 8H), 2.30 (s, 3H, CH₃ 3-acetate), 2.80-3.05 (m, 2H), 4.40 (broad s, 1H, H17), 5.75 (broad s, 1H), 6.04 (broad s, 1H), 6.80 (broad s, 1H, H4), 6.84 (broad s, 1H, H2), 7.29 (d, 1H, H1), mp: 120.7° C.

Example 2

Preparation of a Compound of Formula (I) Wherein P¹ is t-Butyldimethylsilyl According to an Embodiment of the Invention Step 1: 3,17-di-t-butyldimethylsiloxy-estra-1,3,5(10)-16-tetraene-17-ol To a solution of estrone (50 g, 0.185 mole) and 2,6-lutidine (62 g, 0.58 mole) in dichloromethane 400 ml was added drop wise t-butyl-dimethylsilyl-triflate (102.6 g, 0.39 mole). The solution was stirred at room temperature for 6 hours. Water (300 ml) was added and the organic layer was washed with a diluted solution of sodium carbonate. The dichloromethane solution was partially evaporated and ethyl acetate was added. Diisopropyl ether was added to this solution. The mixture was stirred for 2 hours at 0° C. The precipitate was collected by filtration and dried. 83 g of the title compound were obtained (90% yield).

¹HNMR (CDCl₃) δ 0.20 (s, 12H, (CH₃)₂—Si—), 0.90 (s, 3H, CH₃ at C-18), 0.95 (s, 9H, (CH₃)₃—C—Si—), 1.00 (s, 9H, (CH₃)₃—C—Si—), 1.20-2.40 (m, 11H), 2.75-2.95 (m, 2H), 4.48 (m, 1H, H16), 6.58 (broad s, 1H, H4), 6.62 (dd, 1H, H2), 7.12 (d, 1H, H1), mp: 97.6° C.

Step 2: 3-t-butyldimethylsiloxy-estra-1,3,5(10)-15-tetraene-17-one

To a solution of 3,17-di-t-butyldimethylsiloxy-estra-1,3,5(10)-16-tetraene-17-ol 83 g (0.166 mole) in 400 ml of acetonitrile was added Pd(OAc)₂ 3.8 g (0.017 mole) in an oxygen atmosphere. The mixture was stirred at 40° C. for 12 hours then filtered through a pad of celite. A diluted solution of sodium carbonate was added and the mixture was extracted with ethyl acetate.

After concentration, diisopropyl ether was added and the mixture was stirred at 0° C. for one hour. The product (54.7 g, 86% yield) was collected by filtration and used in the next step without further purification.

¹HNMR (CDCl₃) δ 0.20 (s, 6H, (CH₃)₂—Si—), 1.00 (s, 9H, (CH₃)₃—C—Si—), 1.13 (s, 3H, CH₃ at C-18), 1.20-2.70 (m, 11H), 2.80-3.00 (m, 2H), 6.10 (dd, 1H, H15), 6.58 (broad s, 1H, H4), 6.62 (dd, 1H, H2), 7.11 (d, 1H, H1), 7.63 (dd, 1H, H16), mp: 165° C.

Step 3: 3-t-butyldimethylsiloxy-estra-1,3,5(10)-15-tetraene-17-ol

The collected material (54.7 g, 0.143 mole) was dissolved in THF 300 ml and a solution of cerium chloride heptahydrate (53.3 g, 0.143 mole) in methanol (300 ml) was added. The mixture was cooled to 0° C. sodium borohydride (8.12 g, 0.213 mole, 1.5 eq) was added portion wise keeping the temperature below 9° C. At this end of the addition the mixture was stored for one hour then quenched by addition of a 2N HCl solution (100 ml). The solution was partly evaporated in situ and water (4 L) was added. The precipitate was collected by filtration and dried. After crystallization from a mixture of ethanol/diisopropyl ether the product was collected by filtration and dried. It weighted 46.6 g (85% yield).

¹HNMR (CDCl₃) δ 0.20 (s, 6H, (CH₃)₂—Si—), 0.89 (s, 3H, CH₃ at C-18), 1.00 (s, 9H, (CH₃)₃—C—Si—), 1.20-2.40 (m, 10H), 2.75-2.95 (m, 2H), 4.40 (broad s, 1H, H17), 5.65-5.75 (m, 1H), 5.95-6.10 (m, 1H), 6.57 (broad s, 1H, H4), 6.60 (dd, 1H, H2), 7.13 (d, 1H, H1) mp: 107.5° C.

Example 3

Preparation of a Compound of Formula (I) Wherein P¹ is t-Butyldimethylsilyl According to an Embodiment of the Invention Step 1: 3-t-butyldimethylsiloxy-estra-1,3,5(10)-triene-17-one To a solution of estrone (100 g, 0.37 mole) in 400 ml of dichloromethane, imidazole (50.36 g, 0.74 mole) and t-butyl-dimethylsilyl chloride (61.3 g, 0.41 mole) were added The solution was stirred at room temperature for 24 hours. Then water (200 ml) was added. The organic layer was partially evaporated and diisopropyl ether added. The white solid formed was collected by filtration and dried. It weighted 135.2 g, yield 95%, mp 172° C.

¹HNMR (CDCl₃) δ 0.20 (s, 6H, (CH₃)₂—Si—), 0.90 (s, 3H, CH₃ at C-18), 1.00 (s, 9H, (CH₃)₃—C—Si—), 1.20-2.60 (m, 13H), 2.75-2.95 (m, 2H), 5.65-5.75 (m, 1H), 6.58 (broad s, 1H, H4), 6.63 (dd, 1H, H2), 7.12 (d, 1H, H1) mp: 171.6° C.

Step 2: 3-t-butyldimethylsiloxy-estra-1,3,5(10)-16-tetraene-17-acetate 3-t-butyldimethylsiloxy-estra-1,3,5(10)-triene-17-one 135 g (0.351 mole) were poured in 600 ml of isopropenyl acetate and 12 g of para-toluene-sulfonic acid. The mixture was refluxed. Acetone and isopropenyl acetate were continuously distilled off until the internal temperature reached 98° C. Then the mixture was cooled to 0° C. and potassium carbonate added. After one hour at 0° C. the mixture was filtered. The resulting solution was partially concentrated and diisopropyl ether added. The precipitate was collected by filtration and crystallized from a mixture of ethyl acetate and heptane. The product was collected by filtration and dried. It weighted 119.5 g (yield 80%).

Step 3: 3-t-butyldimethylsiloxy-estra-1,3,5(10)-15-tetraene-17-one

To a solution of 3-t-butyldimethylsiloxy-estra-1,3,5(10)-16-tetraene-17-acetate 119.5 g (0.280 mole) in acetonitrile (1500 ml) were added 27.2 g (0.085 mole of tributyltin methoxide, 11.2 g (0.05 mole) of palladium acetate and 64 ml (0.560 mole) of allyl methyl carbonate. The mixture was refluxed for 2 hours then cooled to room temperature and filtered through a pad of silica gel. The mixture was diluted with water and extracted with ethyl acetate. After concentration to one third of the initial volume diisopropyl ether was added and the solution cooled at 0° C. for one hour.

The product was collected by filtration. It weighted 91 g (85% yield) and was used in the next step without further purification.

$^1$HNMR (CDCl$_3$) δ 0.20 (s, 6H, (CH$_3$)$_2$—Si—), 1.00 (s, 9H, (CH$_3$)$_3$—C—Si—), 1.13 (s, 3H, CH$_3$ at C-18), 1.20-2.70 (m, 11H), 2.80-3.00 (m, 2H), 6.10 (dd, 1H, H15), 6.58 (broad s, 1H, H4), 6.62 (dd, 1H, H2), 7.11 (d, 1H, H1), 7.63 (dd, 1H, H16), mp: 165° C.

Step 4: 3-t-butyldimethylsiloxy-estra-1,3,5(10)-15-tetraene-17-ol

The reduction step was performed as described in step 3 of example 2: the collected material was dissolved in THF and a solution of cerium chloride heptahydrate (1 eq) in methanol was added. The mixture was cooled to 0° C. sodium borohydride (1.5 eq) was added portion wise keeping the temperature below 9° C. At this end of the addition the mixture was stored for one hour then quenched by addition of a 2N HCl solution. The solution was partly evaporated in situ and water was added. The precipitate was collected by filtration and dried. After crystallization from a mixture of ethanol/diisopropyl ether the product was collected by filtration and dried.

$^1$HNMR (CDCl$_3$) δ 0.20 (s, 6H, (CH$_3$)$_2$—Si—), 0.89 (s, 3H, CH$_3$ at C-18), 1.00 (s, 9H, (CH$_3$)$_3$—C—Si—), 1.20-2.40 (m, 10H), 2.75-2.95 (m, 2H), 4.40 (broad s, 1H, H17), 5.65-5.75 (m, 1H), 5.95-6.10 (m, 1H), 6.57 (broad s, 1H, H4), 6.60 (dd, 1H, H2), 7.13 (d, 1H, H1) mp: 107.5° C.

Example 4

Step 2 of Example 1 was repeated using different reagent and reactions conditions as listed in Table 1. 3-acetoxy-estra-1,3,5(10),15-tetraen-17-one was obtained. The yields and conversion rates are given in Table 1.

TABLE 1

| Pd(OAc)$_2$ | Other reagents | Reaction conditions | Conversion rate (%) | Isolated Yield (%) |
|---|---|---|---|---|
| 1.36 eq | | THF, ACN, CH$_2$Cl$_2$, RT | ≈90 | 18 |
| 0.08 eq | Allylmethyl carbonate (1.8 eq) tributyltin methoxide (0.3 eq) | ACN, 70° C. | ≈70 | 24 |
| 0.3 eq | Cu(OAc)$_2$ (1 eq); O$_2$ | ACN, THF, 50° C. | 30 | ND |
| 0.1 eq | O$_2$ | DMSO, 80° C. | ≈70 | ND |
| 0.15 eq | O$_2$ | DMSO, CH$_2$Cl$_2$, 35° C. | 80 | ND |

THF: tetrahydrofuran; ACN acetonitrile; RT: room temperature; DMSO: dimethylsulfoxide; ND not determined.

Example 5

Step 2 of Example 2 was repeated using different reagent and reactions conditions as listed in Table 2. 3-t-butyldimethylsiloxy-estra-1,3,5(10)-15-tetraene-17-one was obtained. The yields and conversion rates are given in Table 2.

TABLE 2

| Pd(OAc)$_2$ | Other reagents | Reaction conditions | Conversion rate (%) | Isolated Yield (%) |
|---|---|---|---|---|
| 1.4 eq | | THF, RT | ≈90 | ND |
| 0.1 eq | O$_2$ | DMSO, CH$_2$Cl$_2$, 35° C. | ≈100 | 71 |
| 0.1 eq | Cu(OAc)$_2$; O$_2$ | DMSO, CH$_2$Cl$_2$, 35° C. | ≈100 | 64 |
| 0.1 eq | Air | DMSO, CH$_2$Cl$_2$, 35° C. | ≈95 | 65 |
| 0.1 eq | O$_2$ | DMSO, CH$_2$Cl$_2$, 35° C. | ≈100 | 93 |

THF: tetrahydrofuran; ACN acetonitrile; RT: room temperature; DMSO: dimethylsulfoxide; ND not determined.

It is to be understood that although preferred embodiments and/or materials have been discussed for providing embodiments according to the present invention, various modifications or changes may be made without departing from the scope and spirit of this invention.

The invention claimed is:

1. A process for the preparation of a compound of formula (I)

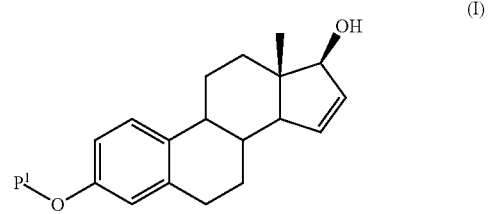

said process comprising the steps of
a) reacting a compound of formula (II), with a silylating agent to produce a compound of formula (III), wherein P$^1$ is R$^2$—Si—R$^3$R$^4$, and P$^2$ is R$^2$—Si—R$^3$R$^4$, wherein R$^2$, R$^3$ and R$^4$ are each independently a group selected from C$_{1-6}$alkyl or phenyl, each group being optionally substituted by one or more substituents independently selected from fluoro or C$_{1-4}$alkyl;

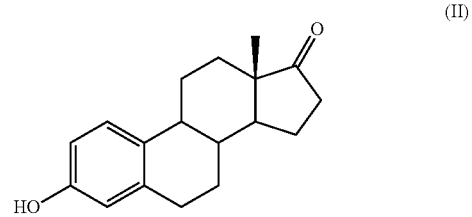

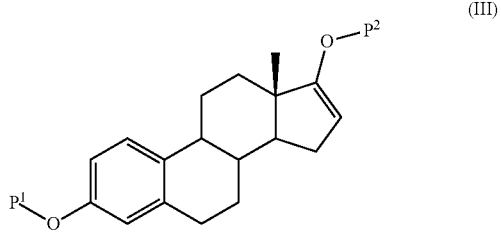

b) reacting the compound of formula (III) in the presence of palladium acetate or palladium chloride to produce a compound of formula (IV); and

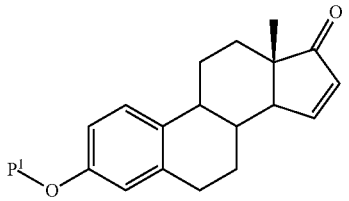

c) reacting the compound of formula (IV) with a reducing agent to produce the compound of formula (I).

2. The process according to claim 1, wherein the silylating agent is selected from the group comprising $C_{1-6}$alkylsilylchloride, $C_{1-6}$alkylsilyltriflate, phenylsilyl chloride, phenylsilyltriflate, $C_{1-6}$alkylphenylsilylchloride, $C_{1-6}$alkylphenylsilyltriflate, each group being optionally substituted by one or more substituents independently selected from fluoro or $C_{1-4}$alkyl.

3. The process according to claim 1, wherein step (b) is performed in the presence of a $C_{1-6}$alkylene carbonate and an organotin compound.

4. The process according to claim 1, wherein said palladium acetate or palladium chloride is present in stoichiometric amounts.

5. The process according to claim 1, wherein said reaction is performed with palladium acetate or palladium chloride present in catalytic or sub-stoichiometric amounts.

6. The process according to claim 1, wherein the reducing agent in step (c) is selected from the group of metal hydride compounds.

7. The process according to claim 6, wherein the metal hydride compound is selected from the group consisting of $NaBH_4/CeCl_3$, $LiAlH_4$, $NaBH_4$, $NaBH(OAc)_3$, and $ZnBH_4$.

8. A process for the preparation of estetrol, said process comprising preparing a compound of formula (I) by a process,

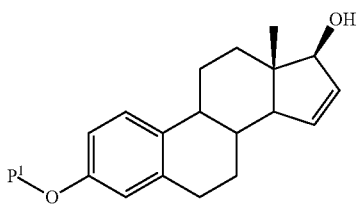

said process comprising the steps of a) reacting a compound of formula (II), with a silylating agent to produce a compound of formula (III), $P^1$ is $R^2$—Si—$R^3R^4$, and $P^2$ is $R^2$—Si—$R^3R^4$, wherein $R^2$, $R^3$ and $R^4$ are each independently a group selected from $C_{1-6}$alkyl or phenyl, each group being optionally substituted by one or more substituents independently selected from fluoro or $C_{1-4}$alkyl;

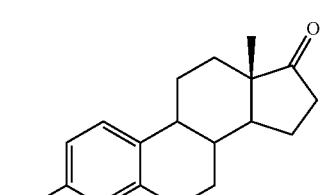

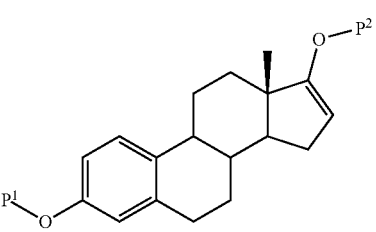

b) reacting the compound of formula (III) in the presence of palladium acetate or palladium chloride to produce a compound of formula (IV); and

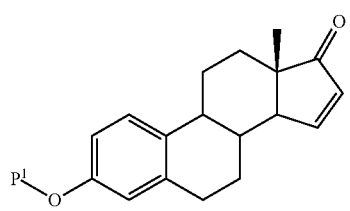

c) reacting the compound of formula (IV) with a reducing agent to produce the compound of formula (I), and further reacting the compound of formula (I) to produce the estetrol.

9. The process according to claim 5, wherein said reaction is performed in an oxygen atmosphere.

* * * * *